United States Patent
Morishima

(10) Patent No.: US 10,165,683 B2
(45) Date of Patent: *Dec. 25, 2018

(54) APPARATUS AND METHODS FOR VIA CONNECTION WITH REDUCED VIA CURRENTS

(71) Applicant: Micron Technology, Inc., Boise, ID (US)

(72) Inventor: Atsushi Morishima, Sagamihara (JP)

(73) Assignee: Micron Technology, Inc., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/854,598

(22) Filed: Dec. 26, 2017

(65) Prior Publication Data

US 2018/0192517 A1    Jul. 5, 2018

Related U.S. Application Data

(63) Continuation of application No. 15/399,664, filed on Jan. 5, 2017, now Pat. No. 9,888,574.

(51) Int. Cl.
  *H05K 1/11* (2006.01)
  *H05K 1/02* (2006.01)
  *H05K 1/18* (2006.01)

(52) U.S. Cl.
  CPC .......... *H05K 1/115* (2013.01); *H05K 1/025* (2013.01); *H05K 1/181* (2013.01); *H05K 1/114* (2013.01); *H05K 2201/0776* (2013.01); *H05K 2201/0979* (2013.01); *H05K 2201/09227* (2013.01); *H05K 2201/09309* (2013.01); *H05K 2201/09609* (2013.01)

(58) Field of Classification Search
  USPC ........................ 361/760, 761, 748
  See application file for complete search history.

(56) References Cited

U.S. PATENT DOCUMENTS

| | | |
|---|---|---|
| 2005/0219009 A1 | 10/2005 | Logothetis et al. |
| 2008/0143379 A1 | 6/2008 | Norman |
| 2008/0289865 A1* | 11/2008 | Nakamura ............. H05K 1/162 174/260 |

OTHER PUBLICATIONS

U.S. Appl. No. 15/399,664, entitled "Apparatus and Methods for Via Connection With Reduced Via Currents", filed Jan. 5, 2017; pp. all.

* cited by examiner

*Primary Examiner* — Andargie M Aychillhum
(74) *Attorney, Agent, or Firm* — Dorsey & Whitney LLP

(57) ABSTRACT

Apparatuses and methods including conductive vias of a printed circuit board are described. An example apparatus includes a first layer including a first conductive plate; a component on the first layer, a second layer including a second conductive plate that may be coupled to an external power source; a third layer between the first layer and the second layer, the third layer including a third conductive plate; a first via coupling the first conductive plate to the second conductive plate; and a second via coupled to the first conductive plate. The first conductive plate includes a first portion coupled to the first via and the first conductive plate further includes a second portion coupled to the second via between the first portion and the component. The second via is coupled to either the second conductive plate or the third conductive plate.

16 Claims, 11 Drawing Sheets

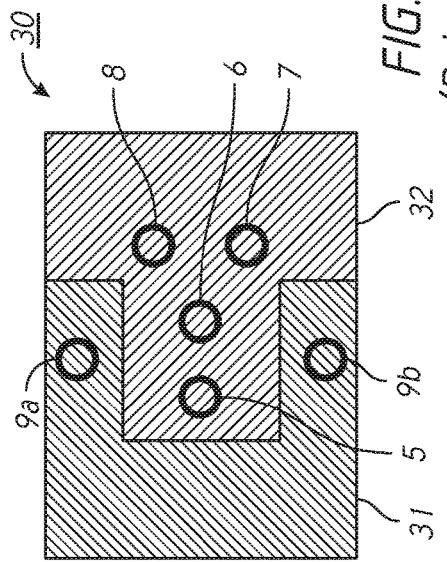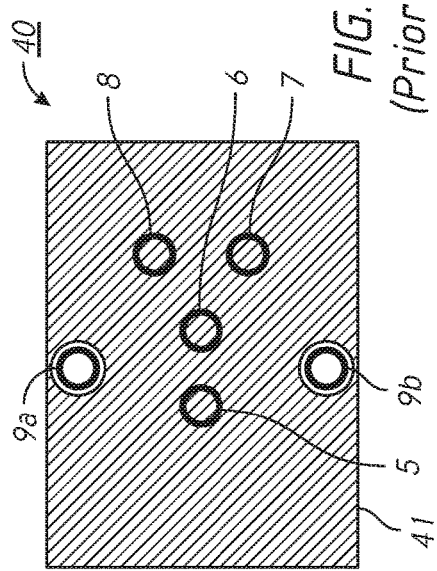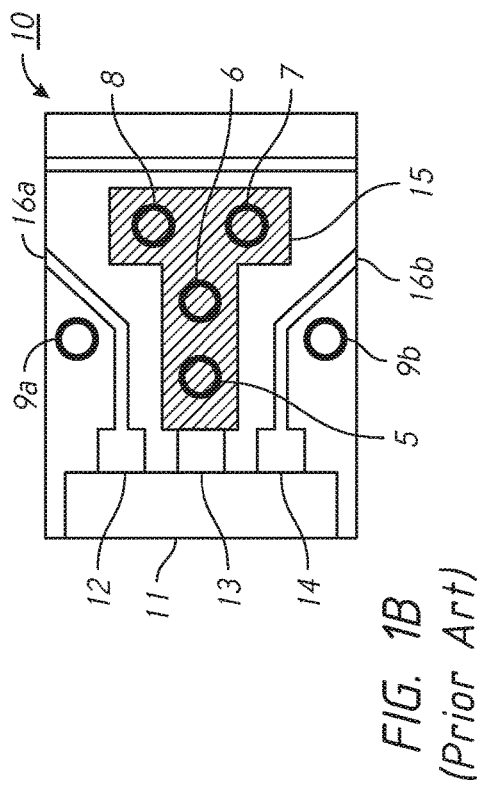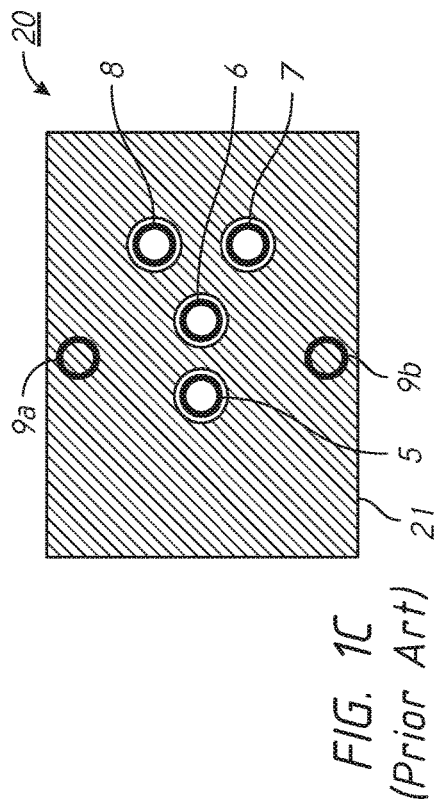

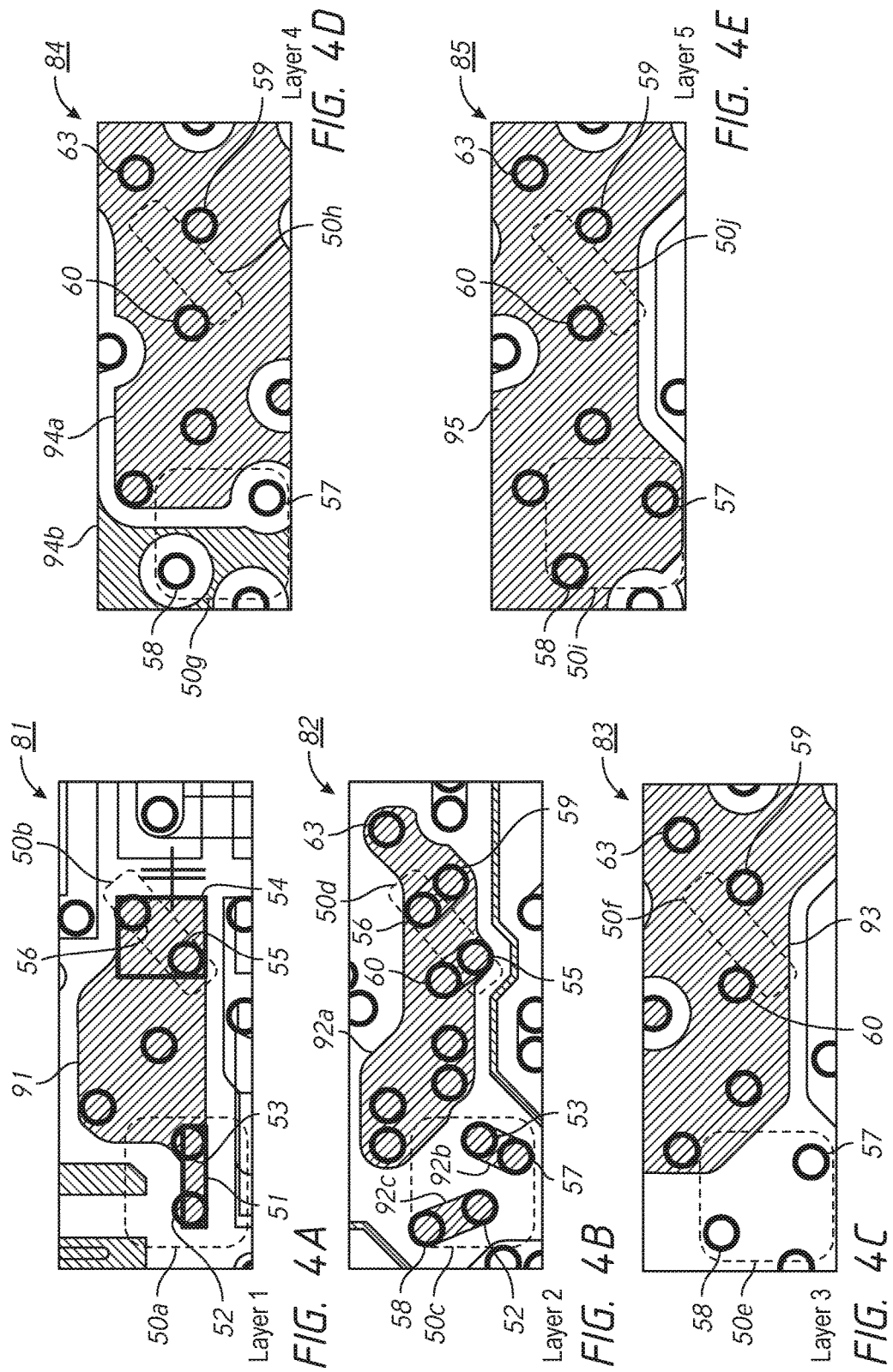

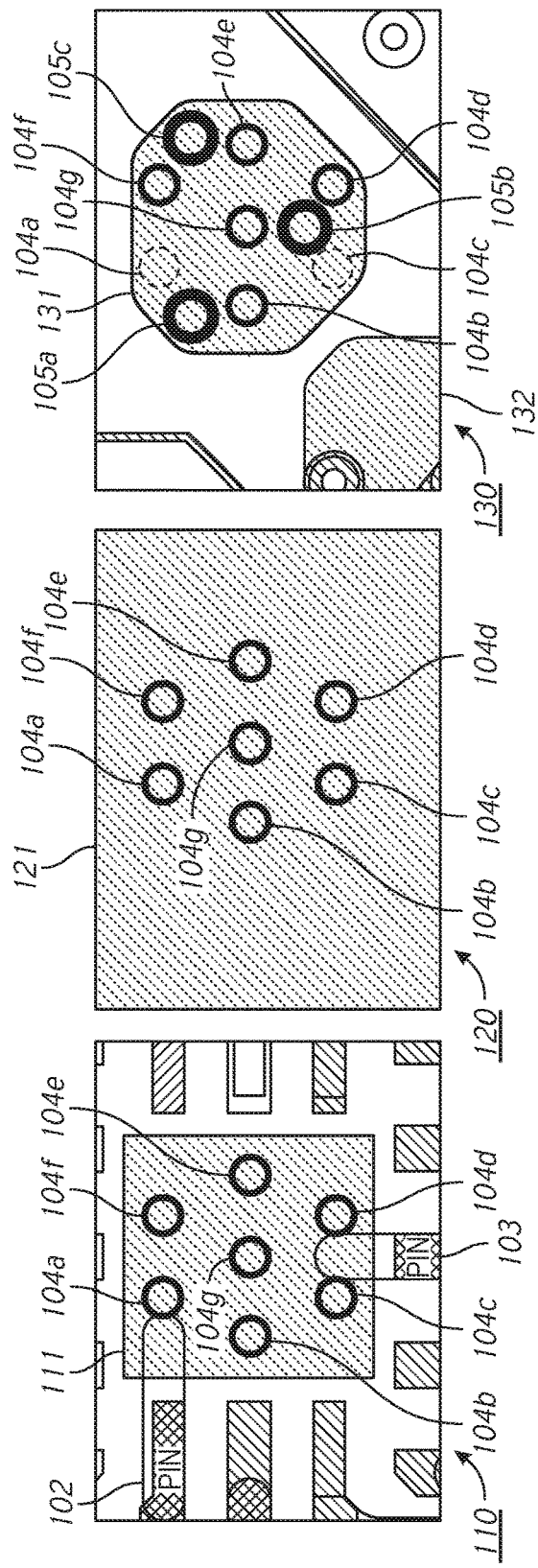

US 10,165,683 B2

APPARATUS AND METHODS FOR VIA CONNECTION WITH REDUCED VIA CURRENTS

CROSS REFRENCE TO RELATED APPLICATIONS)

This application is a continuation of U.S. patent application Ser. No. 15/399,664, filed Jan. 5,2017 and issued as U.S pat. No. 9,888,574 on Feb. 6,2018. The aforementioned application and issued patent, are incorporated herein by reference, in their entirety, and for any purposes.

BACKGROUND

High data reliability, high speed of processing and data access, and reduced apparatus size are features that are demanded from electronic apparatuses. In recent years, there has been an effort to reduce a size of a printed circuit board inside electronic devices. As part of that effort to reduce the size, the printed circuit board may be manufactured to include multiple circuit layers of integrated circuits and surface components densely mounted or embedded.

When a size is reduced, a plurality of vias for power supply across layers of the printed circuit board may be densely located in each layer. Typically, the plurality of vias may be coupled to a power supply pin of an electronic component to supply power to the electronic component, and the plurality of vias may be located around the power supply pin of the electronic component. If one via of the plurality of vias may be located closer to the power supply pin among the plurality of vias, an impedance of a path (e.g., wiring, etc.) between the power supply pin and the one via may be lower which causes a higher current stressed on the path that leads to overheat or damage to surrounding components on the printed circuit board. In order to prevent such overheat or damage, a layout of the printed circuit board was designed to include the plurality of vias for power supply having a substantially equal electrical distance from the power supply pin in a manner that impedances between the power supply pin and the plurality of vias become substantially the same. However, the plurality vias with the substantially equal impedance by using the same wiring, located at the same distance from the power supply pin on a same layer may cause an obstacle for optimization of mounting a number of components densely on a limited space of the printed circuit board.

Another attempt to prevent such overheat or damage was to provide a layout of the printed circuit board with arrangements of power voltage supply regions on layers. FIG. 1A is a schematic diagram of a conventional printed circuit board 1 including a plurality of layers 10, 20, 30 and 40 and a plurality of vias 5 to 8. FIGS. 1B-1E are simplified layout diagrams of the plurality of layers 10, 20, 30 and 40 of the conventional printed circuit board 1. In particular, FIG. 1A is a side view of the printed circuit board 1 including the plurality of vias 5 to 8 coupled to a power voltage supply region 15 which provides a power supply voltage to a power supply pin 13 of an electronic component 11. The plurality of vias 5 to 8 are coupled to power voltage supply regions 32 and 41 on the layers 30 and 40, which maintain the same power voltage. Vias 9a and 9b are coupled to other voltage supply region 21 and 31 on the layers 20 and 30, which may function as a negative power supply (e.g., ground). The electronic component 11 also includes pins 12 and 14 on sides of the power supply pin 13, which transmit and receive other signals through wirings 16a and 16b. An area where the vias 5-8 are arranged is surrounded by wirings 16a and lob. Because of the wirings 16a and 16b coupled to the pins 12 and 14, the vias 6-8 and the via 5 cannot be arranged at an equal distance from the power supply pin 13, which cannot avoid the concentration of current into the via 5.

Thus, a different optimizing scheme for locating a plurality of vias to be coupled to a power supply pin may be desired.

BRIEF DESCRIPTION OF THE DRAWINGS

FIGS. 1B-1E are simplified layout diagrams of the plurality of layers of the conventional printed circuit board.

FIGS. 4A-4E are simplified layout diagrams of a plurality of layers of a printed circuit board in accordance with an embodiment of the present disclosure.

FIGS. 5A-5C are simplified layout diagrams of a plurality of layers of a printed circuit board in accordance with an embodiment of the present disclosure.

DETAILED DESCRIPTION OF PREFERRED EMBODIMENTS

Various embodiments of the present disclosure will be explained below in detail with reference to the accompanying drawings. The following detailed description refers to the accompanying drawings that show, by way of illustration, specific aspects and embodiments in which the present invention may be practiced. These embodiments are described in sufficient detail to enable those skilled in the art to practice the present invention. Other embodiments may be utilized, and structure, logical and electrical changes may be made without departing from the scope of the present invention. The various embodiments disclosed herein are not necessary mutually exclusive, as some disclosed embodiments can be combined with one or more other disclosed embodiments to form new embodiments.

Figure 1A:
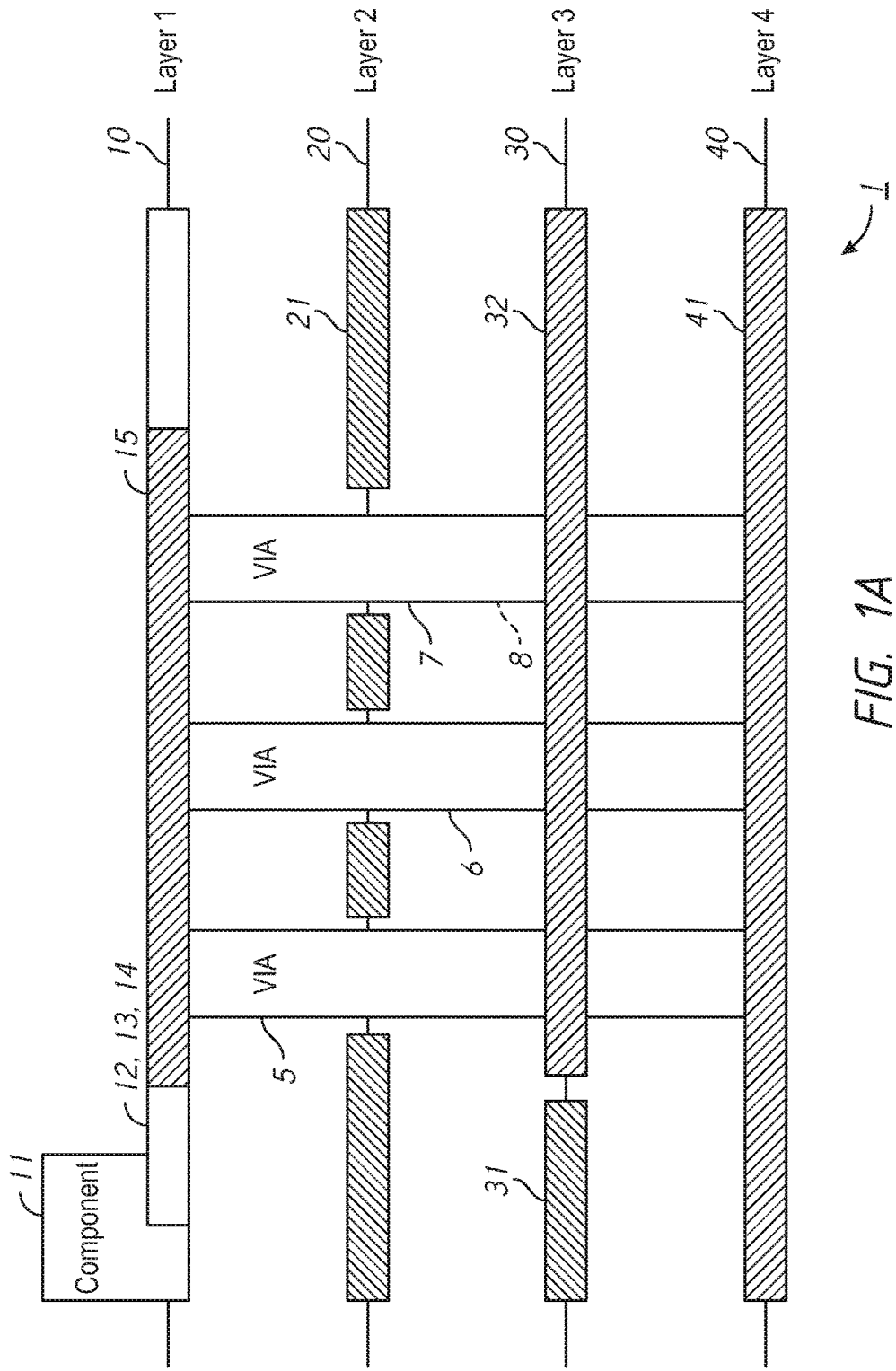
FIG. 1A is a schematic diagram of a conventional printed circuit board including a plurality of layers and a plurality of vias.
Figure 2A:
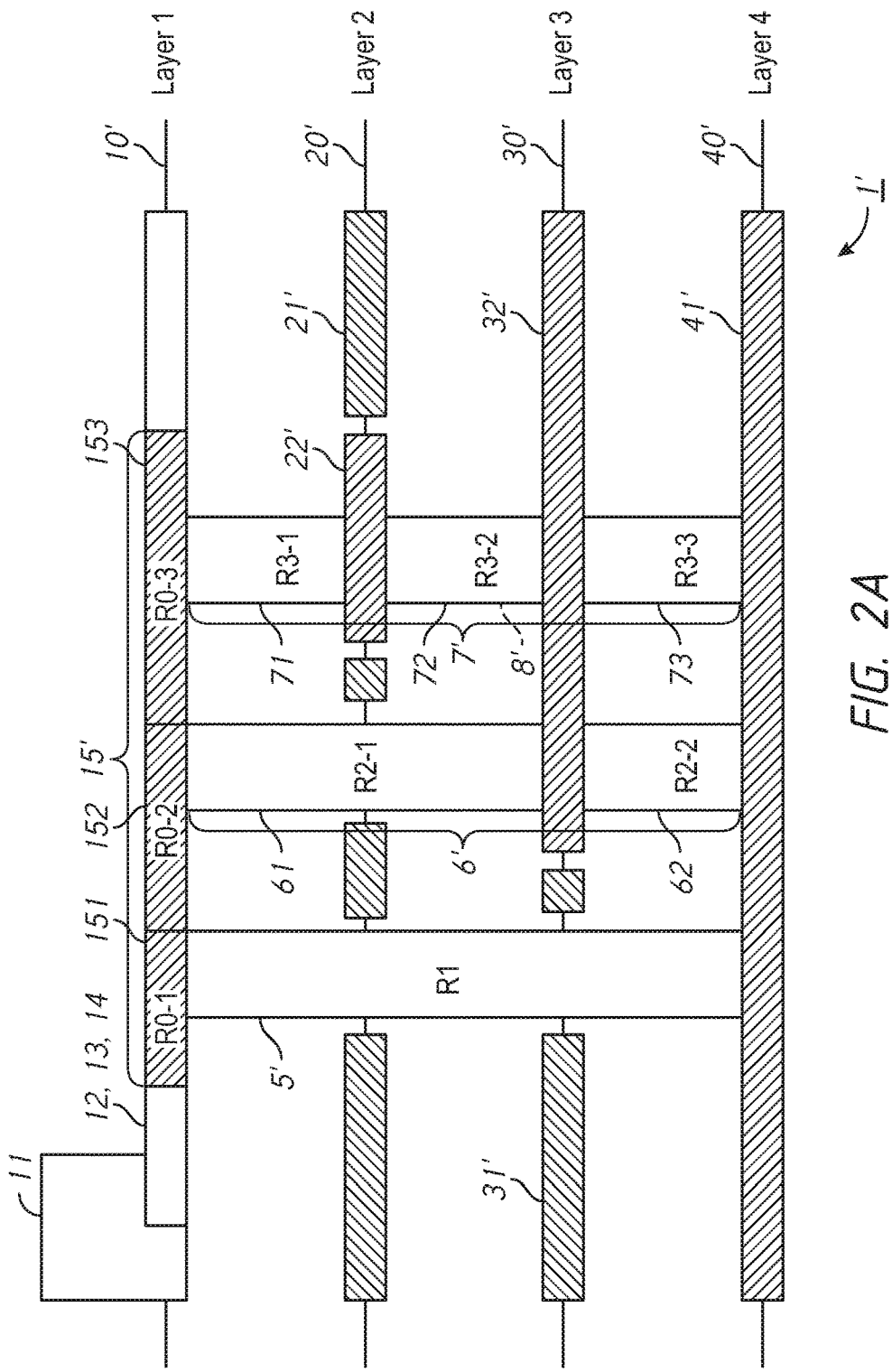
FIG. 2A is a schematic diagram of a printed circuit board including a plurality of layers and a plurality of vias in accordance with an embodiment of the present disclosure.

FIG. 2A is a schematic diagram of a printed circuit board 1' including a plurality of layers 10', 20', 30' and 40' and a plurality of vias 5' to 8' in accordance with an embodiment of the present disclosure. FIG. 2A is a side view of the printed circuit board 1' including the plurality of vias 5' to 8', where via 8' is hidden by via 7'. For example, a number of the plurality of layers (e.g., planes) 10', 20', 30' and 40' may be stacked to each other at different levels in the printed circuit board 1' as a multi-level plane structure. For example, the layer 20' may include one side in contact with the layer 10' and the other side in contact with the layer 30'. This example may include four layers; however, the number of the plurality of layers may not be limited to four. For example, the layer 10' may include a component 11 mounted on the layer 10'. For example, the component 11 may be a semiconductor device, which receives a power voltage and consumes power. The component 11 may have pins 12, 13 and 14 that may be coupled to other components on the layer 10'. For example, the pins 12 and 14 may be coupled to components (not shown) via wirings 16a and 16b, respectively. The layer 10' may include a first voltage supply region 15'. For example, the first voltage supply region 15' may be a conductive plate (e.g., a metal plate) to provide a first voltage (e.g., a power voltage). The pin 13 may be located in a first portion of the first voltage supply region 15' and the pin 13 may be coupled to the first voltage supply region 15'. Thus, the pin 13 may receive the first voltage from the first voltage supply region 15' and provide the first voltage to the component 11. The vias 6', 7' and 8' are located in a second portion of the first voltage supply region 15'. The second portion of the first voltage supply region 15' is located away from the first portion to be electrically insulated from the pins 12 and 14 as well as wirings around the pins 12 and 14. The via 5' may be located in a third portion of the first voltage supply region 15', where the third portion of the first voltage supply region 15', between the first portion and the second portion of the first voltage supply region 15'. The via 5' may be located in relatively close proximity to the pin 13. The via 6' may be located further from the component 11, located opposite to the pin 13 with respect to the via 5', having the via 5' between the via 6' and the pin 13.

Figure 2B:
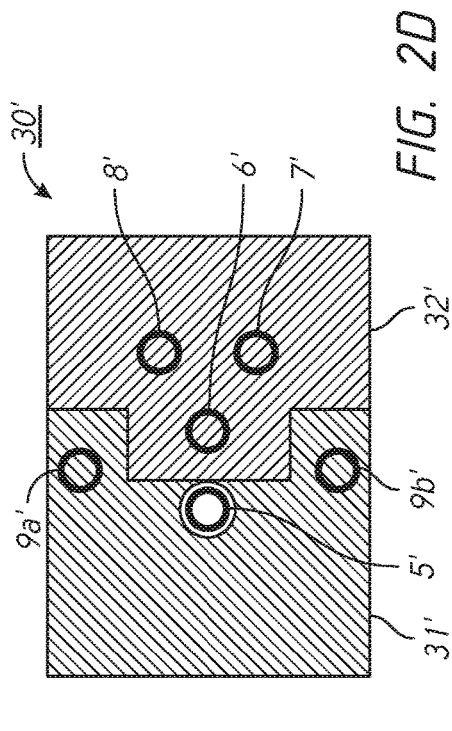
FIGS. 2B-2E are simplified layout diagrams of the plurality of layers of the printed circuit board in accordance with an embodiment of the present disclosure.
Figure 2C:
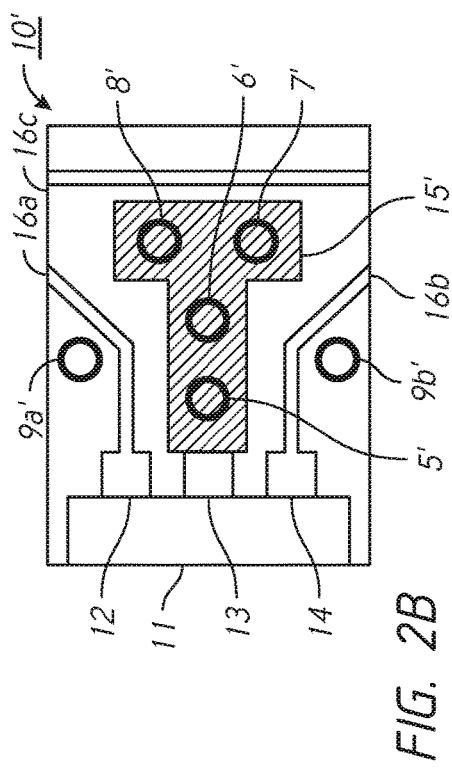
Figure 2D:
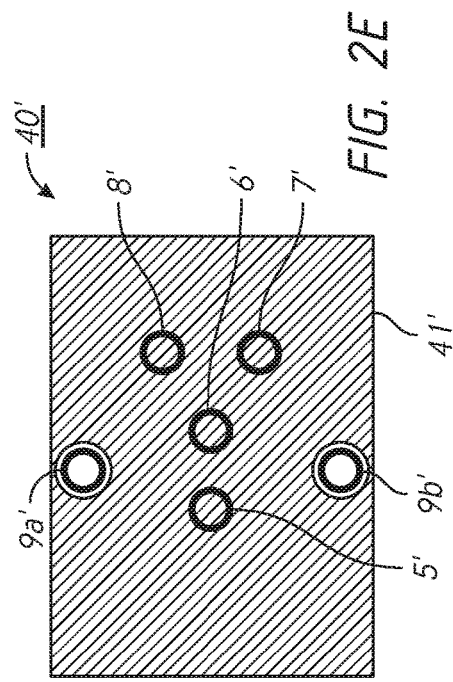

FIGS. 2B-2E are simplified layout diagrams of the plurality of layers 10', 20', 30' and 40' of the printed circuit board 1' in accordance with an embodiment of the present disclosure. In FIG. 2B, the first voltage supply region 15' may be restricted by the wirings 16a, 16b and a wiring 16c which may be coupling other components (not shown). The plurality of vias 5' to 8' are located in the first voltage supply region 15' and may be coupled to the first voltage supply regions 15' and 41', which supply the first voltage, on the layers 10' and 40' respectively. In addition to vias 6' and 7', the via 8' may be located in the second portion of the first voltage supply region 15'.

The plurality of vias 5' to 8' may also be coupled to the first voltage supply regions 22' and 32' on the layers 20' and 30', respectively for supplying the first voltage. The first voltage may be provided by an external power source (not shown) to one of the first voltage supply regions 22', 32' and 41'. For example, the external power source may provide the first voltage to the first voltage supply region 41' on the layer 40' and the first voltage can be provided through the vias 5' to 8' to the first voltage supply region 15' on the layer 10'. Thus, the first voltage supply region 15' may provide the first voltage to the component 11 from the pin 13.

For example, the via 5' may be coupled to the first voltage supply regions 15' and 41', however, the via 5' may be located away from (e.g., outside) the first voltage supply regions 22' and 32', respectively. The via 5' may be located in second voltage supply regions 21' and 31' for supplying a second voltage (e.g., a ground voltage) on the layers 20' and 30', respectively, however, the via 5' may be electrically insulated from the second voltage supply regions 21' and 31'. The via 6' may be coupled to the first voltage supply regions 15', 32' and 41', however, the via 6' may be located away from (e.g., outside) the first voltage supply region 22'. The via 6' may be located in the second voltage supply region 21', however, the via 6' may be electrically insulated from the second voltage supply region 21'. The vias 7' and 8' may be coupled to the first voltage supply regions 15', 22', 32' and 41'. Including more than one vias 7' and 8' coupled to the first voltage supply regions 15', 22', 32' and 41' for increased conductivity may alleviate a current load to the via 5'.

Figure 2E:
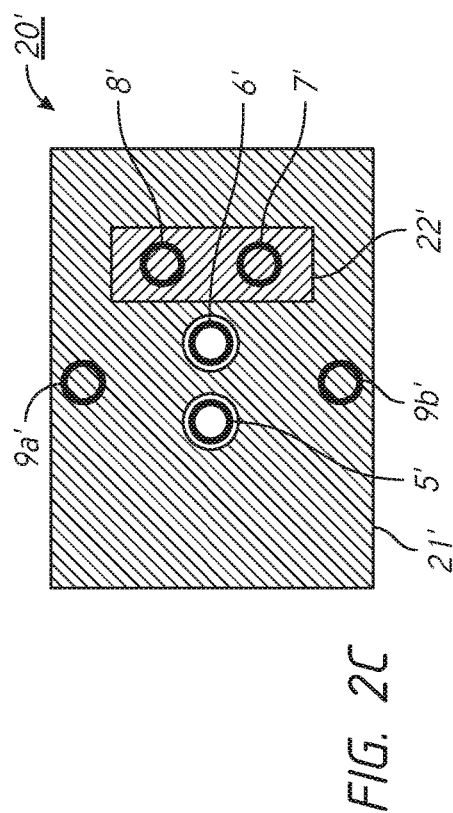

Vias 9a' and 9b' located away from (e.g., outside) the first voltage supply region 15'. The vias 9a' and 9b' may be located inside the second voltage supply regions 21' and 31' and coupled to the second voltage supply regions 21' and 31'. For example, the second voltage may be provided by coupling the second voltage supply regions 21' and 31' to a ground line (not shown). As shown in FIG. 2E, the vias 9a' and 9b' may be electrically insulated from the first voltage supply region 41'. For example, the first voltage supply regions 15' 22', 32' and 41' and the second voltage supply regions 21' and 31' may be made of conductive material. The first voltage supply region and the second voltage supply region on the same layer may be insulated by non-conductive material between the first voltage supply region and the second voltage supply region.

Figure 2F:
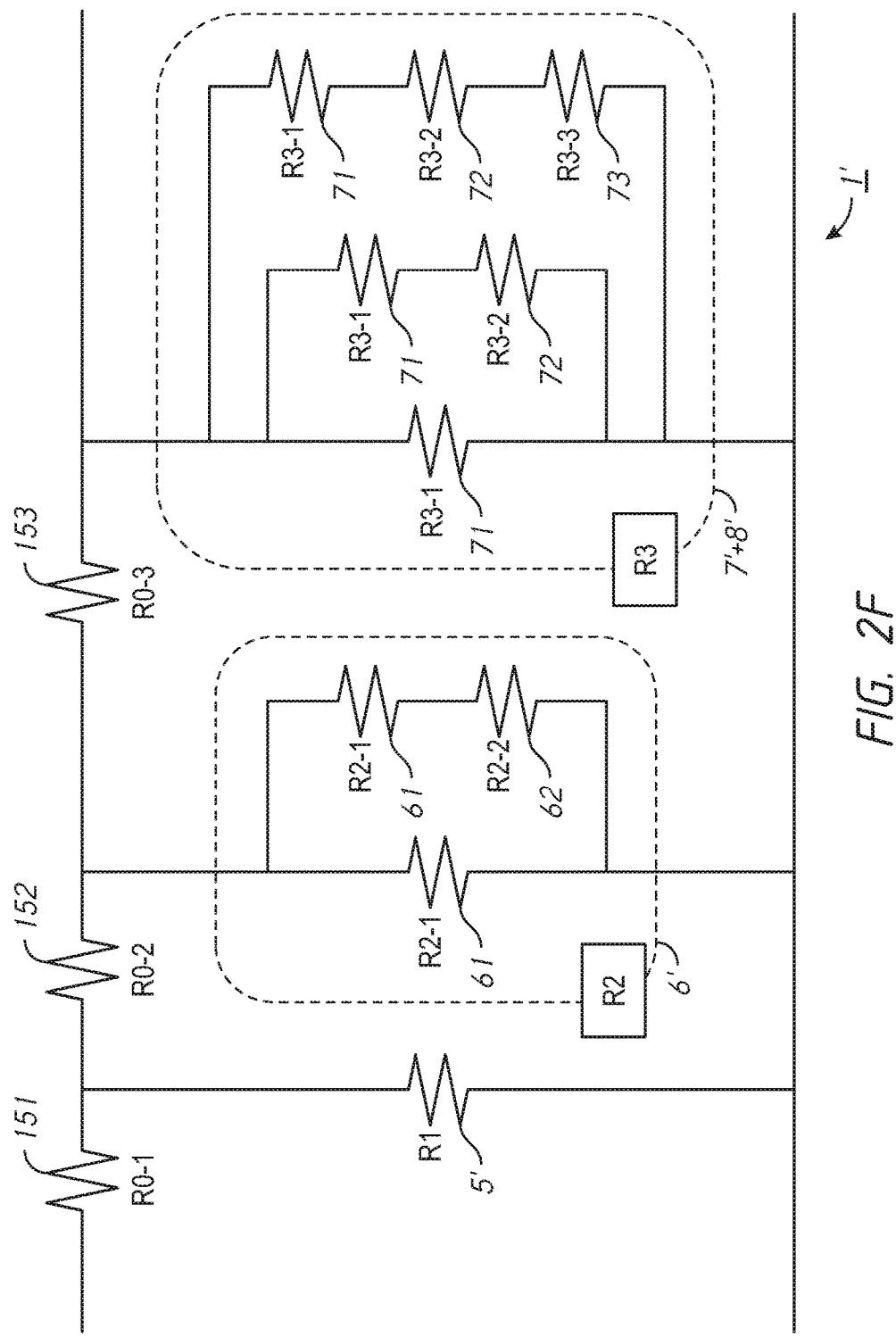
FIG. 2F is a circuit diagram of the printed circuit board including the plurality of vias in accordance with an embodiment of the present disclosure.

FIG. 2F is a circuit diagram of the printed circuit board 1' including the plurality of vias 5' to 8' in accordance with an embodiment of the present disclosure. For example, the circuit diagram of FIG. 2F shows an approximation circuit that models impedances of the printed circuit board 1', including the first voltage supply region 15' and the vias 5' to 8'. For example, the first voltage supply region 15' may be approximated as impedance portions R0-1 151, R0-2 152 and R0-3 153. The impedance portion R0-1 151 may be impedance between the pin 13 of the component 11 and the via 5', the impedance portion R0-2 152 may be impedance between the via 5' and the via 6', and the impedance portion R0-3 153 may be impedance between the via 6' and the vias 7' and 8', as shown in FIG. 2A. The via 5' coupled to the first voltage supply regions 15' and 41' on the layers 10' and 40' may be approximated as an impedance R1. Thus, a first electrical path from the pin 13 and the first voltage supply region 41' on the layer 40' through the via 5' may have an impedance (R0-1+R1). The via 6' coupled to the first voltage supply regions 15', 32' and 41' on the layers 10', 30' and 40' may have an impedance R2. Thus, a second electrical path from the pin 13 and the first voltage supply region 41' on the layer 40' through the via 6' may have an impedance (R0-1+R0-2+R2). The impedance R2 may be due to an impedance portion R2-1 61 between the first voltage supply regions 15' and 32' on the layers 10' and 30', respectively, and an impedance portion R2-2 62 between the first voltage supply regions 32' and 41' on the layers 30' and 40', respectively. Thus, the impedance R2 in via 6' may be approximated as a parallel circuit of the impedance portion R2-1 61 and a serial circuit of the impedance portions R2-1 61 and R2-2 62. The vias 7' and 8' coupled to the first voltage supply regions 15', 22', 32' and 41' on the layers 10', 20' 30' and 40' may have an impedance R3. Thus, a third electrical path from the pin 13 and the first voltage supply region 41' on the layer 40' through the vias 7' and 8' may have an impedance (R0-1+R0-2+R0-3+R3). The impedance R3 may be due to an impedance portion R3-1 71 between the first voltage supply regions 15' and 22' on the layers 10' and 20', respectively, an impedance portion R3-2 72 between the first voltage supply regions 22' and 32' on the layers 20' and 30', respectively and an impedance portion R3-3 73 between the first voltage supply regions 32' and 41' on the layers 30' and 40', respectively. Thus, the impedance R3 in the vias 7' and 8' may be approximated as a parallel circuit of the impedance portion R3-1 71, a serial circuit of the impedance portions R3-1 71 and R3-2 72, and a serial circuit of the impedance portion R3-1 71, R3-2 72 and R3-3 73. In this configuration, a total impedance of the approximation circuit may satisfy conditions as follows.

$$R0\text{-}1+R1>R0\text{-}1+R0\text{-}2+R2>R0\text{-}1+R0\text{-}2+R0\text{-}3+R3 \quad (1)$$

$$1/R2=1/R2\text{-}1+1/(R2\text{-}1+R2\text{-}2) \quad (2)$$

$$1/R3=1/R3\text{-}1+1/(R3\text{-}1+R3\text{-}2)+1/(R3\text{-}1+R3\text{-}2+R3\text{-}3) \quad (3)$$

As shown in Expression (1), a current on the via 5' may be reduced, if the impedance on the first electrical path is greater than the impedances on the second and third electrical paths. Expression (2) represents relationships between the impedances related to the via 6'. Expression (3) represents relationships between the impedances related to the vias 7' and 8'. From the above Expression (1), the impedance on the first electrical path may be configured to be greater than the impedances on the second and third electrical paths, even though an impedance portion (R0-1+R0-2) of the first voltage supply regions 151 and 152, defined by the component 11 and a node where the via 6' is coupled to the first voltage supply region 152, is greater than an impedance portion (R0-1) of the first voltage supply region 151, defined by the component 11 and a node where the via 5' is coupled to the first voltage supply region 151.

Figure 3A:
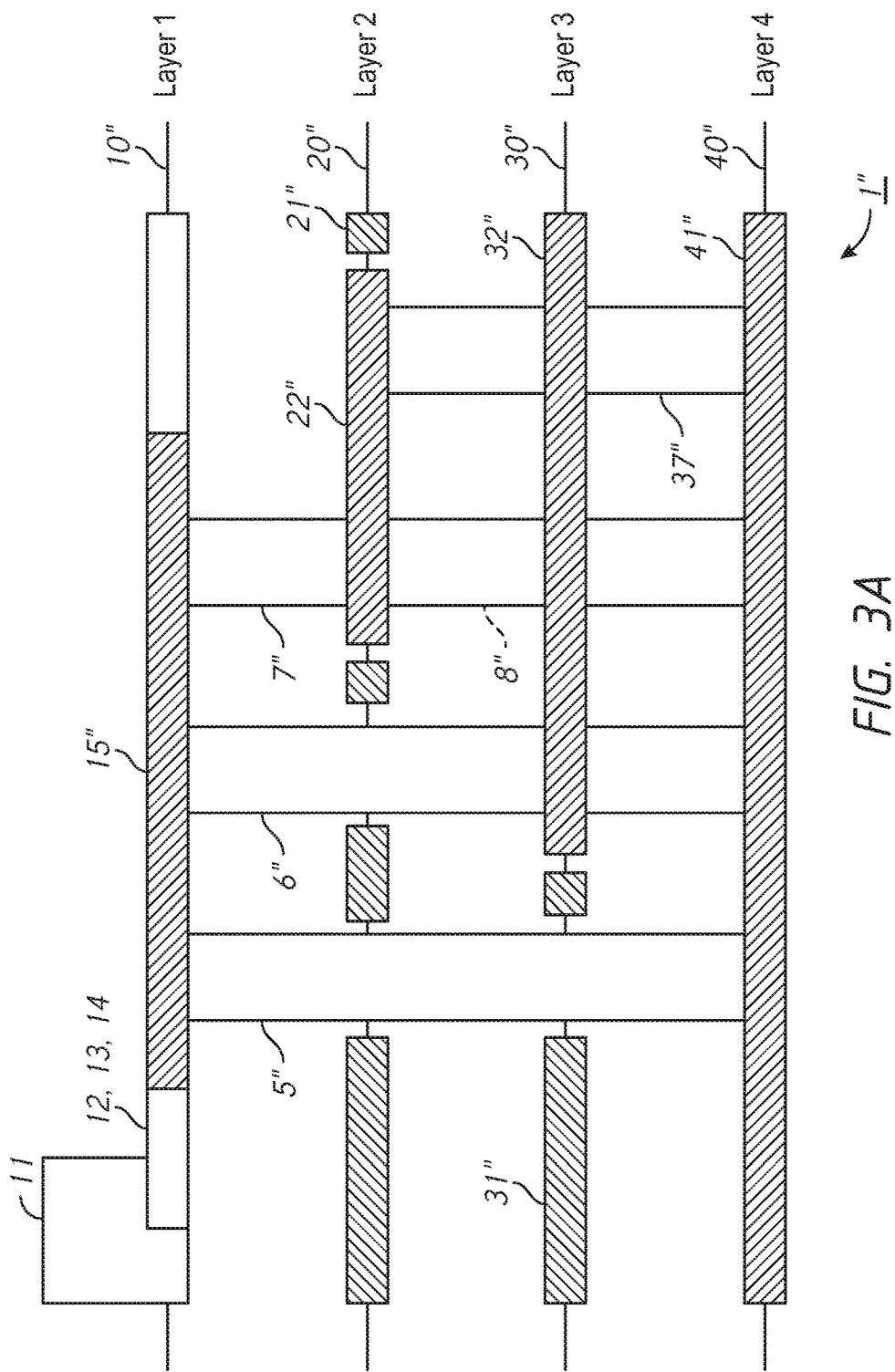
FIG. 3A is a schematic diagram of a printed circuit board including a plurality of layers and a plurality of vias in accordance with an embodiment of the present disclosure.
Figure 3B:
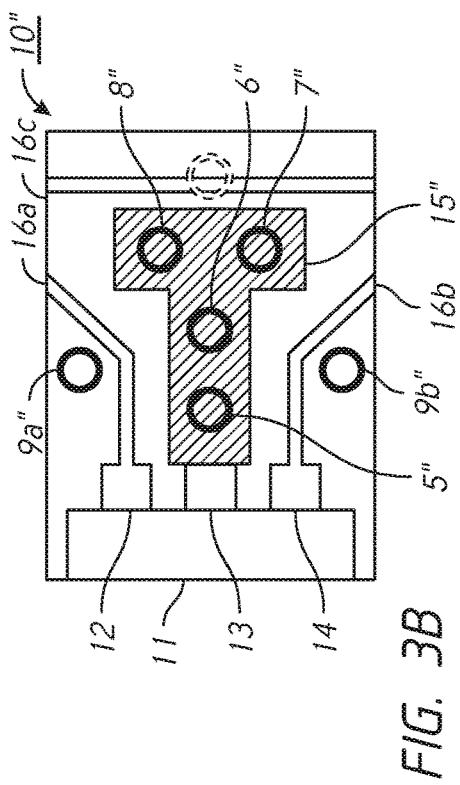
FIGS. 3B-3E are simplified layout diagrams of the plurality of layers of the printed circuit board in accordance with an embodiment of the present disclosure.
Figure 3D:
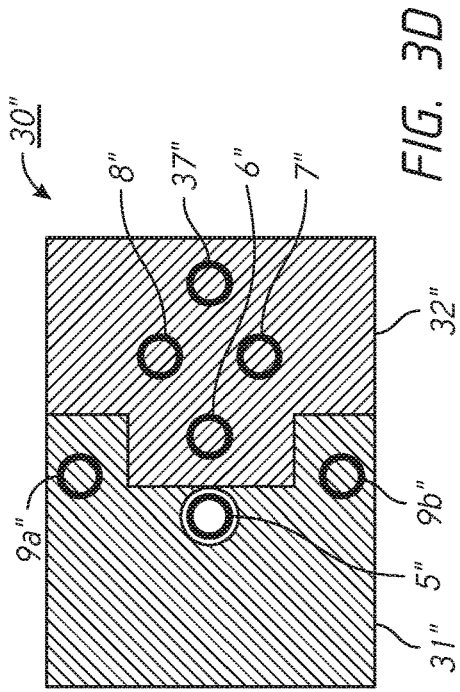
Figure 3C:
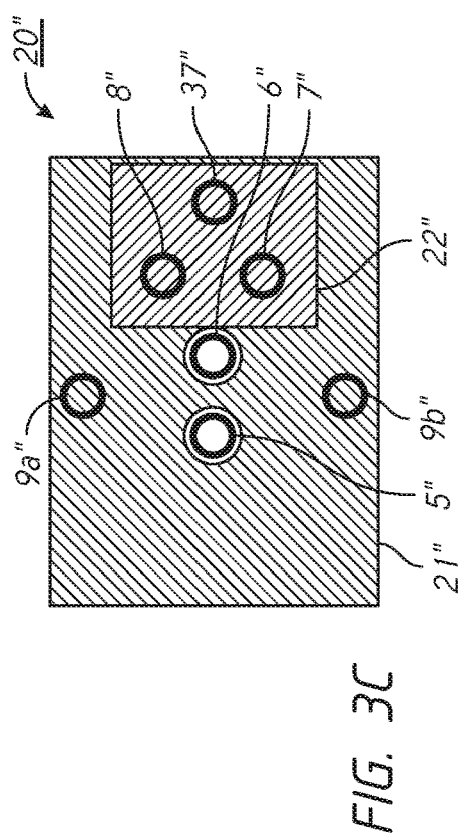
Figure 3E:
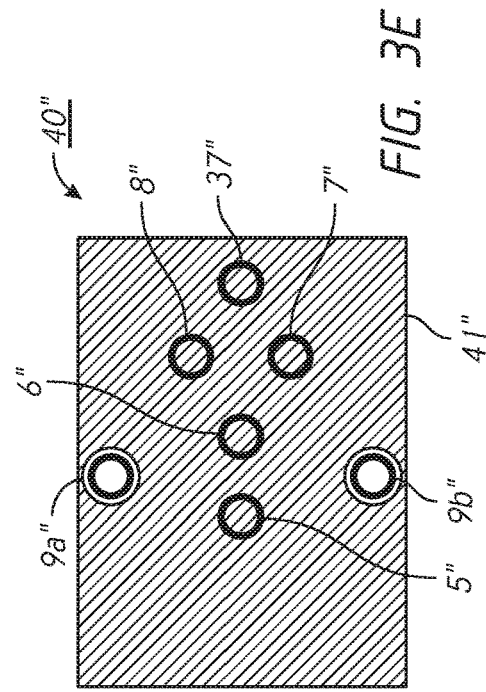

FIG. 3A is a schematic diagram of a printed circuit board 1" including a plurality of layers 10", 20", 30" and 40" and a plurality of vias in accordance with an embodiment of the present disclosure. FIGS. 3B-3E are simplified layout diagrams of the plurality of layers 10", 20", 30" and 40" of the printed circuit board 1" in accordance with an embodiment of the present disclosure. FIG. 3A is a side view of the printed circuit board 1" including the plurality of vias 5" to 8" and 37". Description of components 5" to 8", 10", 20", 30" and 40" in FIG. 3A corresponding to components 5' to 8', 10', 20', 30' and 40' included in FIG. 2A will not be repeated and changes from FIG. 2A including positional and coupling relationships between the components will be described. The printed circuit board 1" further includes a via 37". The via 37" may be excluded and thus electrically insulated from any region of the layer 10". The via 37" may be located in the first voltage supply regions 22", 32" and 41" on the layers 20", 30" and 40", respectively and coupled to the first voltage supply regions 22", 32" and 41". The via 37" may be located at a side opposite to the component 11, farther than vias 5" to 8". For example, the via 37" may be located opposite to the via 5" with respect to the vias 6", 7" and 8" on the layers 20", 30" and 40". For example, the via 37" may be located opposite to the via 5" with respect to the vias 6", 7" and 8" in the first voltage supply region 41". Including the via 37" increases conductivity of the vias away from the via 5", and thus increases currents on vias 7" and 8".

FIGS. 4A-4E are simplified layout diagrams of a plurality of layers 81-85 of a printed circuit board in accordance with an embodiment of the present disclosure. FIG. 4F is a schematic diagram of the printed circuit board including the plurality of layers and the plurality of vias in accordance with an embodiment of the present disclosure. FIG. 4F is a side view of the plurality of layers 81-85, including the plurality of vias 52,53 and 55-60. The layers 81-85 may be stacked to each other in the listed order, as shown in FIG. 4F.

For example, the layer 82 may include one side in contact with the layer 81 and the other side in contact with the layer 83. In FIG. 4A, the layer 81 may include a first voltage supply region 91 that may be a conductive plate (e.g., a metal plate) to provide a first voltage (e.g., a power voltage). For example, the first voltage supply region 91 may be coupled to a component 51 in a first portion 50a of the layer 81 and a component 54 in a second portion 50b of the layer 81. The first portion 50a of the first voltage supply region 91 may include vias 52 and 53 coupled to the first voltage supply region 91. The first portion 50a of the layer 81 may provide the first voltage to the component 51. The second portion 50b of the first voltage supply region 91 may include vias 55 and 56 coupled to the first voltage supply region 91. The second portion 50b of the first voltage supply region 91 may provide the first voltage to the component 54.

The layer 82 may include first voltage supply regions 92a, 92b and 92c to provide the first voltage. The vias 52 and 53 inside a first portion 50c of the layer 82 corresponding to the first portion 50a of the layer 81 may be coupled to vias 58 and 57 outside the first portion 50c of the layer 82, respectively. The first voltage supply region 92a may be coupled to vias, including the vias 55 and 56 in a second portion 50d of the layer 82 corresponding to the second portion 50b of the layer 81. However, the first voltage supply region 92.a may be decoupled to some vias, including the vias 58 and 57. Instead, the first voltage region 92b may be coupled to the via 57 and the first voltage region 92c may be coupled to the via 58. The first voltage supply region 92a may also include vias 59 and 60 coupled to the vias 56 and 55, respectively. The vias 59 and 60 may be outside the second portion 50d of the layer 82.

The layer 83 may include a first voltage supply region 93 to provide the first voltage. The vias 52, 53, 55 and 56 for coupling the layers 81 and 82 are not included in the layer 83 and decoupled from the first voltage supply region 93. The vias 58 and 57 may be inside a first portion 50e of the layer 83 corresponding to the first portion 50a of the layer 81. The first portion 50e of the layer 83 including the vias 58 and 57 is outside the first voltage supply region 93 and the vias 58 and 57 may be decoupled from the first voltage supply region 93. The first voltage supply region 93 may include vias 59 and 60 coupled to the first voltage supply region 93. The first voltage supply region 93 may include a second portion 50f of the layer 83 corresponding to the first portion 50b of the layer 81. There may be no via included in the second portion 50f of the layer 83.

The layer 84 may include a first voltage supply region 94a to provide the first voltage and a second voltage supply region 94b to provide a second voltage (e.g., a ground voltage). The vias 52, 53, 55 and 56 for coupling the layers 81 and 82 may not be excluded in the layer 84 and thus may be decoupled from the first voltage supply region 94a. The vias 58 and 57 may be inside a first portion 50g of the layer 84 corresponding to the first portion 50a of the layer 81. The first portion 50g of the layer 84 including the vias 58 and 57 may be disposed across a portion of the first voltage supply region 94a where the via 57 is located, and a portion of the second voltage supply region 94b where the via 58 is located. The via 57 may be coupled to the first voltage supply region 94a. The via 58 may be electrically insulated from the second voltage supply region 94b. The first voltage supply region 94a may include vias 59 and 60 coupled to the first voltage supply region 94a. Thus, the first voltage supply region 94a may be decoupled from the vias 58 and 57. The first voltage supply region 94a may include a second portion 50h of the layer 84 corresponding to the first portion 50b of the layer 81. There may be no via included in the second portion 50h of the layer 84.

The layer 85 may include a first voltage supply region 95 to provide the first voltage. For example, the first voltage supply region 95 may be coupled to an external power supply source (not shown), which may provide the first voltage to the first voltage supply region 95. The vias 52, 53, 55 and 56 for coupling the layers 81 and 82 may be excluded in the layer 85 and thus may be decoupled from the first voltage supply region 95. The first voltage supply region 95 may include vias 57, 58, 59 and 60 coupled to the first voltage supply region 95. The vias 58 and 57 may be inside a first portion 50i of the layer 85 corresponding to the first portion 50a of the layer 81. The first voltage supply region 95 may include a second portion 50j of the layer 85 corresponding to the first portion 50b of the layer 81. There may be no via included in the second portion 50j of the layer 85.

Figure 4F:
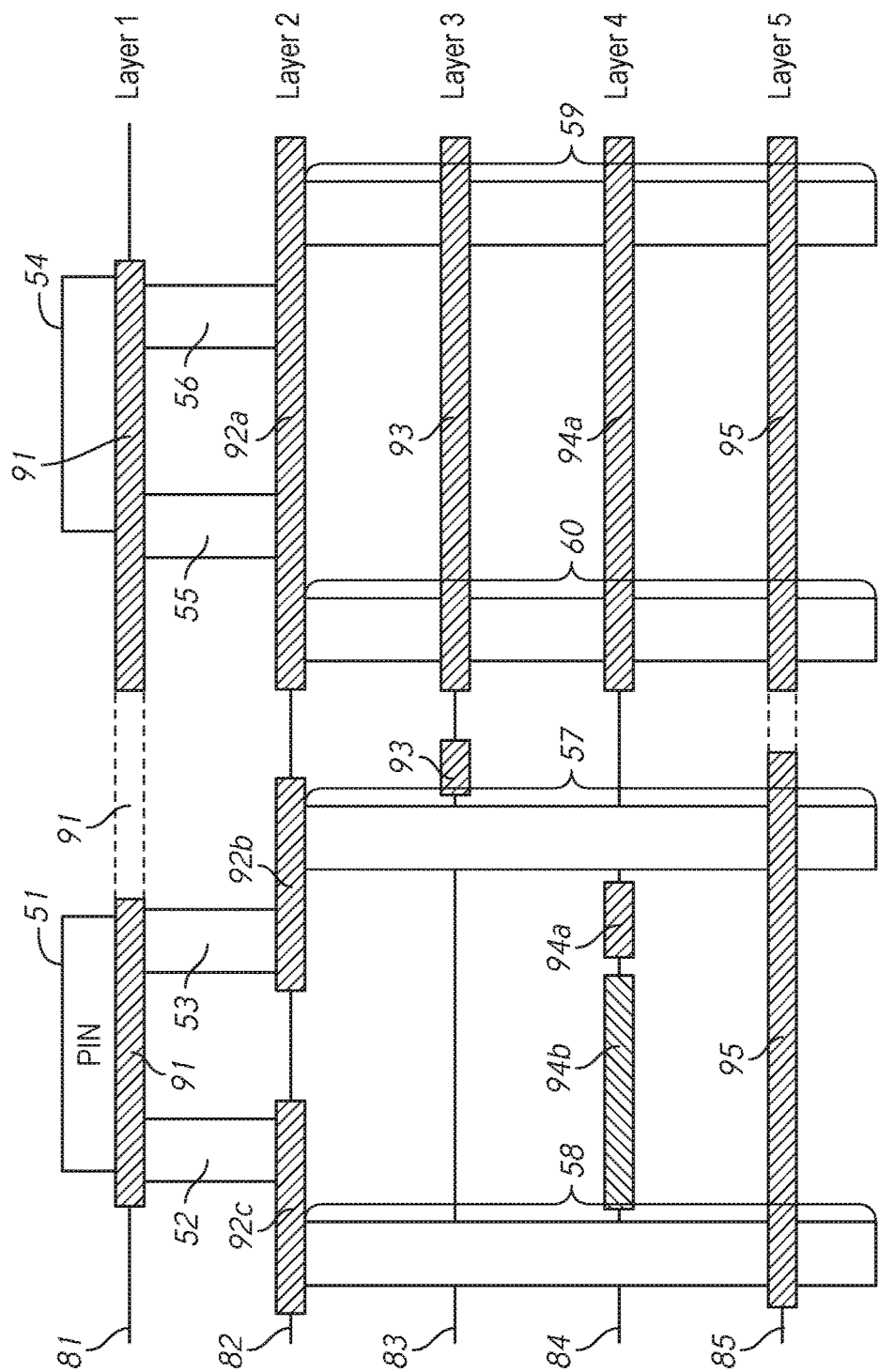
FIG. 4F is a schematic diagram of the printed circuit board including the plurality of layers and the plurality of vias in accordance with an embodiment of the present disclosure.

As shown in FIGS. 4A and 4F, the vias 52, 53, 55 and 56 coupled to the pins 51 and 54 on the layer 81 may be provided the first voltage through the vias 58, 57, 60 and 59, respectively. The vias 58 and 57 coupled to the vias 52 and 53, respectively, may be decoupled from the first voltage supply regions 92a, 93 and 94a on the layer 82, 83 and 84, whereas the vias 60 and 59 coupled to the vias 55 and 56 may be coupled to the first voltage supply regions 92a, 93 and 94a. The vias 52, 53, 55 and 56 may not be directly coupled to the first voltage supply region 95 in the layer 85, thus, currents on the vias 52, 53, 55 and 56 may be suppressed. Further, another via 63 may be included to couple the layers 82, 83, 84 and 85. The via 63 may be included in the first voltage supply plan regions 92a, 93, 94a and 95, and coupled to the first voltage supply plan regions 92a, 93, 94a and 95. Configurations of layers may not be limited to the description above. For example, it is possible to include another layer between any two adjacent layers of the above layers 81 to 85, which does not include a first voltage supply region (e.g., a conductive plate) to provide the first voltage. For example, the pin 51 may be coupled to a component (not shown). The component may be an integrated circuit, which receives a power voltage and consumes power. For example, the pin 54 may be coupled to a first terminal of another component on the layer 81. For example, the other component may have a second terminal coupled to another plate, as shown in FIG. 4A. For example, the other component may be a compensation capacitor.

Figure 5D:
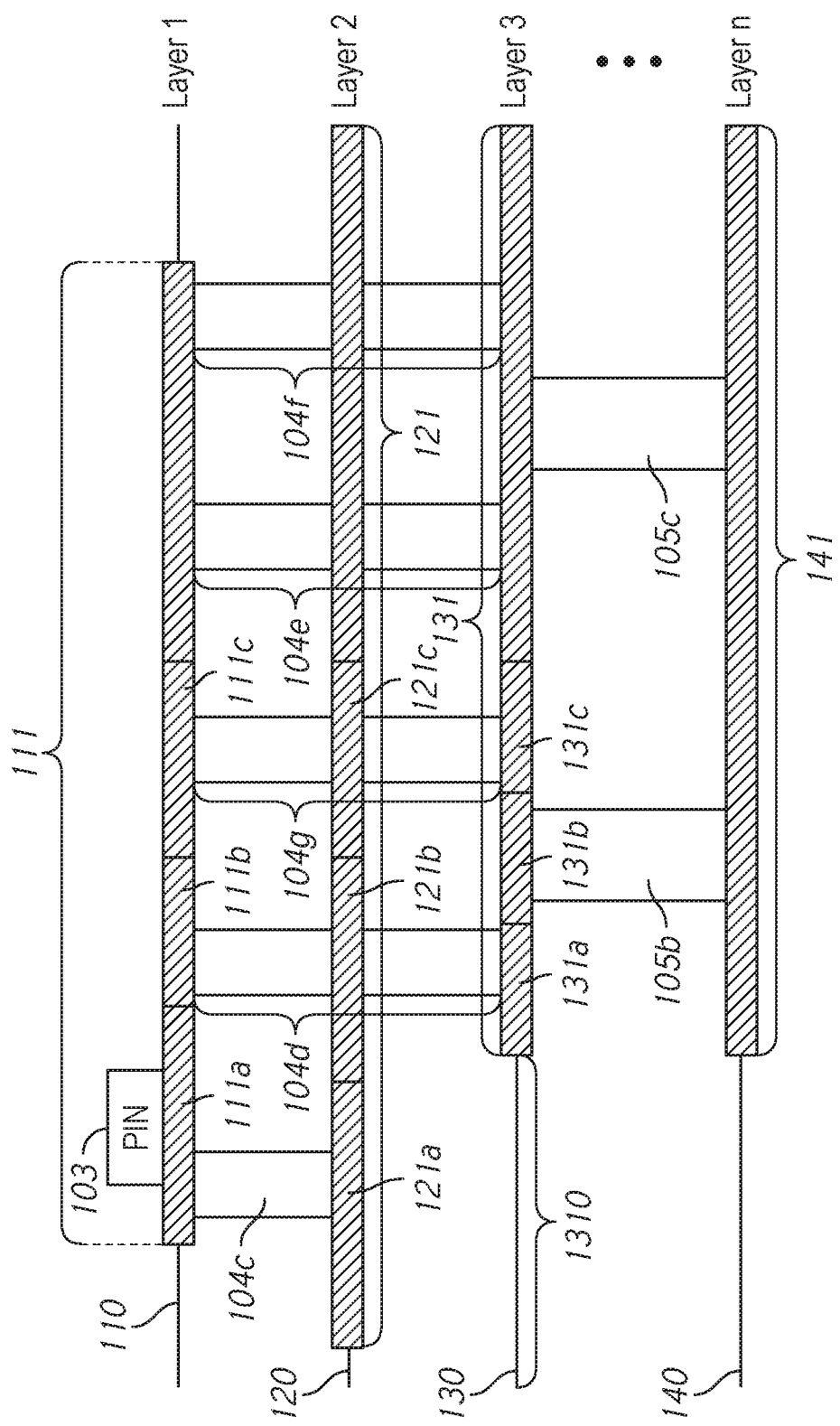
FIG. 5D is a schematic diagram of the printed circuit board including the plurality of layers and the plurality of vias in accordance with an embodiment of the present disclosure.

FIGS. 5A-5C are simplified layout diagrams of a plurality of layers 110, 120 and 130 of a printed circuit board in accordance with an embodiment of the present disclosure. Fin. 5D is a schematic diagram of the printed circuit board including the plurality of layers and the plurality of vias in accordance with an embodiment of the present disclosure. FIG. 5D is a side view of the plurality of layers 110, 120 and 130 including the plurality of vias 104c to 104g, 105b and 105c.

The layers 110, 120 and 130 may be stacked to each other in the listed order. For example, the layer 120 may include one side in contact with the layer 110 and the other side in contact with the layer 130. In FIG. 5A, the layer 110 may include a first voltage supply region 111 that may be a conductive plate (e.g., a metal plate) to provide a first voltage (e.g., a power voltage). For example, the first voltage supply region 111 may be coupled to a component (not shown) on the layer 110. The component may have pins 102 and 103. For example, a portion of the pin 102 and a portion of the pin 103 may be included in the first voltage supply region 111 and coupled to the first voltage supply region 111. The first voltage supply region 111 may include vias 104a to 104g to form a hexagon having the via 104g. For example, the vias 104a to 104g may be located in a manner that the via 104g is at a center of the hexagon, and vias 104a to 104f may be located at vertices of the hexagon, having a same distance from the via 104g and neighbor vias. For example, the via 104a may be at the same distance from the vias 104g, 104b and 104f. For example, the via 104b may be at the same distance from the vias 104g, 104a and 104c. For example, the first voltage supply region 111 may include portions 111a, 111b and 11c. The via 104c may be coupled to the portion 111a of the first voltage supply region 111. For example, the component including the pin 103 may be placed in proximity to the portion 111a of the first voltage supply region 111 and away from the portion 111b of the first voltage supply region 111. The pin 103 may be coupled to the portion 111a of the first voltage supply region 111. The via 104d may be coupled to the portion 111b of the first voltage supply region 111. The via 104g may be coupled to the portion 111c of the first voltage supply region 111. For example, the portion 111b may be between the portion 111c and the pin 103 of the component.

The layer 120 in FIG. 5B may include a first voltage supply region 121 to provide the first voltage. The vias 104a to 104g are inside the first voltage supply region 121. The vias 104a to 104g may be coupled to the first voltage supply region 121. For example, the vias 104a and 104c may be short vias coupling between the first voltage supply regions 111 and 121. For example, the first voltage supply region 121 may include portions 121a, 121b and 121c. The via 104c may be coupled to the portion 121a of the first voltage supply region 121. The via 104d may be coupled to the portion 121b of the first voltage supply region 121. The via 104g may be coupled to the portion 121c of the first voltage supply region 121.

The layer 130 in FIG. 5C may include a first voltage supply region 131 that may be a conductive plate (e.g., a metal plate) to provide a first voltage (e.g., a power voltage) and a second voltage region 132 that may be a conductive plate to provide a second voltage (e.g., a ground voltage). For example, the first voltage supply region 131 may include portions 131a, 131b and 131c. The layer 130 may also include a portion 1310 outside of first voltage supply region 131 and thus insulated from the first voltage supply region 131. For example, the via 104c above the portion 1310 may be isolated (e.g., not in direct contact with) from the first voltage supply region 131. The first voltage supply region 131 may include vias 104b, 104d to 104g and 105a to 105c. For example, the via 104b may be coupled to the via 105a. The via 104d may be coupled to the portion 131a of the first voltage supply region 131. The via 104g may be coupled to the portion 131c of the first voltage supply region 131. For example, the via 105b may be coupled to the portion 131b of the first voltage supply region 131.

As shown in FIGS. 5C and 5D, the vias 104a and 104c may be excluded from the layer 130 and decoupled from the first voltage supply region 131. The first voltage supply region 131 including the vias 105a to 105c may be coupled to an external power external power supply source (not shown), which may provide the first voltage. Alternatively, the vias 105a to 105c may be coupled to another layer, (e.g., Layer n 140 in FIG. 5D) coupled to a first voltage region 141 that may be a conductive plate (e.g., a metal plate) that is coupled to an external power external power supply source (not shown), which may provide the first voltage. For example, a diameter of the vias 105a to 105c may be greater than a diameter of the vias 104a to 104g. In this manner, current loads on vias in close proximity of pins, such as vias 104a and 104c near pins 102 and 103 in FIG. 5A may be reduced to prevent overheat or damage to surrounding components on a printed circuit board.

Although this invention has been disclosed in the context of certain preferred embodiments and examples, it will be understood by those skilled in the art that the inventions extend beyond the specifically disclosed embodiments to other alternative embodiments and/or uses of the inventions and obvious modifications and equivalents thereof. In addition, other modifications which are within the scope of this invention will be readily apparent to those of skill in the art based on this disclosure. It is also contemplated that various combination or sub-combination of the specific features and aspects of the embodiments may be made and still fall within the scope of the inventions. It should be understood that various features and aspects of the disclosed embodiments can be combined with or substituted for one another in order to form varying mode of the disclosed invention. Thus, it is intended that the scope of at least some of the present invention herein disclosed should not be limited by the particular disclosed embodiments described above.

What is claimed is:

1. An apparatus comprising:
a printed circuit board (PCB); and
an electronic component mounted on the PCB,
wherein the PCB comprises:
 a first plane including a first conductive region, and wherein the first conductive region includes a first portion, a second portion and a third portion;
 a second plane including a second conductive region;
 a third plane including a third conductive region,
 a first conductive via between the third portion of the first conductive region and the second conductive region, the first conductive via electrically insulated from the third conductive region of the third plane;
 a second conductive via between the second portion of the first conductive region and the second conductive region; and,
 a third conductive via between the second portion of the first conductive region, the second conductive region, and the third conductive region.

2. The apparatus of claim 1, wherein the electronic component is coupled to the first portion of the first conductive region.

3. The apparatus of claim 2, wherein a pin of the electronic component couples the first portion of the first conductive region to the electronic component.

4. The apparatus of claim 1, wherein the first, second and third planes are disposed at different levels from one another.

5. The apparatus of claim 1, wherein an electrical path between the third portion of the first conductive region and the second conductive region includes the second conductive via and the third conductive region.

6. The apparatus of claim 1, wherein an impedance of the first conductive via is greater than an impedance of the second and third conductive vias.

7. The apparatus of claim 1, further comprising:
a fourth conductive via,
wherein all four of the first through fourth conductive vias are connected to the first conductive region of the first plane, fewer than four of the first through fourth conductive vias are connected to the second conductive region of the second plane, and fewer than three of the first through fourth conductive vias are connected to the third conductive region of the third plane.

8. An apparatus comprising:
a first layer including a first conductive plate;
a second layer including a second conductive plate;
a third layer between the first layer and the second layer, wherein the third layer includes a third conductive plate;
a first via configured to couple the first conductive plate to the second conductive plate and the third conductive plate;
a second via configured to couple the first conductive plate to the second conductive plate, the second via insulated from the third conductive plate; and
a third via configured to couple the second conductive plate to the third conductive plate,
wherein the first conductive plate includes a first portion coupled to the first via and the first conductive plate further includes a second portion coupled to the second via.

9. The apparatus of claim 8, further comprising a component on the first layer, the second portion coupled to the second via between the first portion and the component.

10. The apparatus of claim 8, wherein the second via is decoupled from the third conductive plate.

11. The apparatus of claim 8, wherein the second via is located in the third layer.

12. The apparatus of claim 8, wherein the second conductive plate is configured to be coupled to a voltage source.

13. The apparatus of claim 8, wherein the third via is insulated from the first conductive plate.

14. The apparatus of claim 8, wherein the third via is located opposite to the second via with respect to the first via.

15. The apparatus of claim 8, wherein an impedance of an electrical path in the second via is greater than an impedance of an electrical path in the first via.

16. The apparatus of claim 8, further comprising:
a fourth via,
wherein all four of the first through fourth vias are connected to the first conductive plate, fewer than four of the first through fourth vias are connected to the second conductive plate, and fewer than three of the first through fourth vias are connected to the third plate.

* * * * *